United States Patent [19]

Tsukada et al.

[11] Patent Number: 5,585,255
[45] Date of Patent: Dec. 17, 1996

[54] BILE ACID SULFATE SULFATASE GENE, PLASMID CONTAINING SAID GENE AND METHOD OF PRODUCING BILE ACID SULFATE SULFATASE

[75] Inventors: Yoji Tsukada, Kyoto; Yasuhiko Tazuke, Ashiya; Shigenori Okada; Kenichi Adachi, both of Uji, all of Japan

[73] Assignee: Marukin Shoyu Co., Ltd., Japan

[21] Appl. No.: 140,104

[22] PCT Filed: Feb. 26, 1993

[86] PCT No.: PCT/JP93/00244

§ 371 Date: Oct. 26, 1993

§ 102(e) Date: Oct. 26, 1993

[87] PCT Pub. No.: WO93/17114

PCT Pub. Date: Sep. 2, 1993

[30] Foreign Application Priority Data

Feb. 28, 1992 [JP] Japan .................................. 4-043382

[51] Int. Cl.$^6$ .................................. C12N 9/16; C12N 15/55; C12N 15/63

[52] U.S. Cl. .................. 435/196; 435/320.1; 536/23.2

[58] Field of Search .................... 536/23.7, 23.2; 435/320.1, 240.2, 252.3, 196

[56] References Cited

U.S. PATENT DOCUMENTS 5,091,305  2/1992  Sugimori et al. ................ 435/19
5,100,795  3/1992  Sugimori et al. ................ 435/196

OTHER PUBLICATIONS

Hunkapiller et al., Meth. Enzymol. 91:227–236 (1983).
Lathe, J. Mol. Biol. 183:1–12 (1985).
Mashige et al., Clin. Chem. 27:1352–1356 (1981).

*Primary Examiner*—Robert A. Wax
*Assistant Examiner*—Eric Grimes
*Attorney, Agent, or Firm*—Knobbe Martens Olson & Bear

[57] ABSTRACT

The present invention relates to a bile acid sulfate sulfatase gene coding for the amino acid sequence as shown in FIG. 4 and the gene derived from bacteria which belongs to genus *Pseudomonas testosteroni*, or a bile acid sulfate sulfatase gene as shown in FIG. 3, a plasmid containing the gene, a method for producing a bile acid sulfate sulfatase, and a bile acid sulfate sulfatase.

11 Claims, 4 Drawing Sheets

```
His Asp Gln Asp Asp Arg Gly Gly Ser Gly Ala Lys Ser Pro Ala Val Leu Ala Ala Arg
                                                                              40
Ala Gln Val Phe Lys Ala Asn Pro Gln Met Val Arg Ser Ile Met Glu Gly Gly Gly Phe
                                                                              60
Gly Thr Glu Leu Ser Tyr Ala Val Ala Asn Ser Met Tyr Ser Arg Thr Asp Gln Asn Ala
                                                                              80
Ile Ala Asp Ala Arg Ala Lys Leu Lys Val Glu Ala Val Ala Pro Arg Thr Trp Leu Leu
                                                                             100
Arg Phe Pro Ile Val Asn Val Val Val Phe Glu Thr Asp Glu Gly Leu Val Leu Val Asp
                                                                             120
Ser Gly Tyr Ala Pro Ala Gly Pro Ala Leu Ala Glu Thr Leu Lys Lys Leu Ser Asn Lys
                                                                             140
Pro Leu His Thr Val Ile Leu Thr His Phe His Ala Asp His Ala Phe Gly Ala Trp Ala
                                                                             160
Leu Met Asp Gln Lys Pro His Val Val Thr Glu Gln Arg Phe Ile Ser Gln Met Glu Leu
                                                                             180
Asp Met Arg Ser Asn Gly Leu Ile Ala Arg Asn Asn Gln Gln Ser Val Ala Asp Val Pro
                                                                             200
Arg Thr Trp Ala Asp Ala Val Arg Pro Thr Gln Thr Phe Arg Asp Lys Thr Thr Leu Lys
                                                                             220
Ile Gly Gly Glu Asp Phe Val Leu Thr His Ala Arg Gly Glu Thr Glu Asp Gln Ile Trp
                                                                             240
Val Ala Val Pro Gly Arg Lys Ile Val Ala Ser Ala Asp Tyr Phe Gln Gly Phe Leu Pro
                                                                             260
Asn Ala Gly Asn Gly Lys Arg Arg Gln Arg Tyr Pro Glu Glu Trp Ala Arg Ala Leu Arg
                                                                             280
Asp Met Ala Ala Leu Lys Pro Glu Leu Leu Leu Pro Ala His Gly Pro Ala Ile Thr Lys
                                                                             300
Pro Glu Glu Ile Gln Asp Arg Leu Pro Ala Gln Ala Gln Met Leu Asp Ser Ile Ser Arg
                                                                             320
Gln Val Val Ala Gly Leu Asn Ser Gly Val Arg Arg Asp Gln Val Ile Glu Lys Val Ala
                                                                             340
Leu Pro Pro Glu Leu Ala Arg Arg Ser Asp Ala Arg Glu Leu Tyr Val Ser Ala Lys Asp
                                                                             360
Ile Gly Arg Met Val Val Ser Glu Tyr Ser Gly Trp Trp Asp Asp Ile Pro Ser His Trp
                                                                             380
Arg Pro Ala Ser Leu Ala Asn Glu Ala Lys Glu Ile Val Gln Leu Ala Gly Gly Ala Arg
                                                                             400
Pro Val Ile Gln Arg Ala Val Ala Leu Ala Asp Ser Asn Pro Glu Leu Ala Ser His Leu
                                                                             420
Ala Asp Trp Ala Trp Tyr Ala Asp Ser Asp Thr Glu Val Ala Gln Gly Ala Leu Lys
                                                                             440
Val Tyr Ser Ala Arg Val Ala Lys Pro Leu Pro Thr Gln Glu Val Leu Val Tyr Ala Glu
                                                                             460
His Met Val Arg Leu Gln Leu Lys Leu Asn Glu Leu Asn Ser Thr Arg Ala Ala Ser Ala
                                        467
Ser Gln Ser Ser Lys Ala His
```

S: *Sma* I

P: *Pst* I pUC18 chromosomal DNA

S: *Sma* I      E: *Eco* RI

P: *Pst* I pUC18 chromosomal DNA

FIG. 3

```
                                30                                      60
ATG AAT GCA GCA ATG GCA AAC ATG AGA AAA GTA TCT CGC CTC TCC CGA TAC GCC TTT GCC
                                90                                     120
ACA GCC CTG GCA CTG AGC CAG TTC GGC ACA GGC ACG GCC AAC GCC CAC GAT CAG GAT GAT
                               150                                     180
CGC GGT GGC TCG GGA GCG AAA AGC CCC GCT GTG CTT GCT GCC CGC GCC CAG GTG TTC AAG
                               210                                     240
GCC AAT CCG CAG ATG GTC AGG TCC ATC ATG GAA GGC GGT GGC TTT GGC ACC GAG CTG TCG
                               270                                     300
TAT GCA GTA GCC AAC AGC ATG TAC AGC CGA ACC GAC CAG AAC GCC ATT GCA GAT GCC CGA
                               330                                     360
GCC AAG CTC AAA GTC GAG GCC GTG GCT CCA CGC ACC TGG CTG CTG CGT TTC CCC ATC GTC
                               390                                     420
AAC GTG GTG GTC TTC GAG ACC GAC GAA GGC CTG GTC TTG GTC GAT AGC GGC TAC GCA CCT
                               450                                     480
GCA GGC CCG GCC TTG GCC GAA ACG CTG AAG AAG CTC AGC AAC AAG CCG TTG CAC ACC GTC
                               510                                     540
ATC CTC ACG CAC TTT CAT GCC GAC CAT GCC TTT GGC GCC TGG GCG TTG ATG GAC CAG AAG
                               570                                     600
CCG CAT GTA GTG ACC GAG CAG CGC TTC ATC TCC CAG ATG GAG CTG GAC ATG CGC AGC AAC
                               630                                     660
GGT CTG ATT GCA CGC AAC AAC CAG CAA AGC GTG GCC GAT GTG CCC CGG ACC TGG GCA GAT
                               690                                     720
GCA GTT CGG CCC ACC CAG ACC TTC AGG GAC AAG ACC ACA CTC AAA ATT GGC GGC GAA GAC
                               750                                     780
TTT GTG CTG ACC CAT GCG CGC GGC GAG ACC GAA GAC CAG ATA TGG GTT GCC GTT CCA GGC
                               810                                     840
CGG AAA ATC GTG GCC AGC GCG GAT TAT TTC CAG GGG TTT CTG CCC AAT GCG GGC AAC GGC
                               870                                     900
AAG CGC CGC CAG CGC TAC CCC GAG GAG TGG GCC CGG GCC CTG CGC GAC ATG GCA GCA CTC
                               930                                     960
AAA CCC GAG CTG CTG CTG CCG GCG CAT GGT CCG GCC ATC ACC AAG CCC GAG GAA ATT CAG
                               990                                    1020
GAC CGA CTG CCC GCC CAG GCC CAG ATG CTG GAC AGC ATC TCC AGG CAA GTG GTG GCC GGC
                              1050                                    1080
CTG AAC AGC GGA GTA CGC CGC GAT CAG GTC ATT GAA AAA GTC GCA CTG CCG CCG GAG CTG
                              1110                                    1140
GCC CGG CGA AGC GAT GCA CGC GAG CTA TAT GTG TCT GCC AAA GAC ATA GGC CGC ATG GTG
                              1170                                    1200
GTC AGC GAG TAC AGC GGC TGG TGG GAC GAT ATT CCA TCG CAC TGG CGC CCG GCG TCC CTG
                              1230                                    1260
GCC AAT GAG GCC AAA GAA ATC GTG CAG CTA GCT GGC GGT GCC AGG CCG GTG ATT CAG CGT
                              1290                                    1320
GCA GTG GCG CTG GCA GAC AGC AAT CCG GAG CTG GCC TCC CAT CTG GCC GAC TGG GCC TGG
                              1350                                    1380
TAT GCA GAC AGC GAT GAC ACC GAG GTG GCT CAA GGC GCA CTG AAG GTC TAT TCC GCG CGT
                              1410                                    1440
GTT GCC AAG CCT CTG CCC ACG CAG GAA GTG CTG GTC TAT GCC GAG CAC ATG GTG CGC CTG
                              1470                                    1500
CAG CTC AAG CTC AAT GAG CTG AAC AGC ACA CGC GCG GCC AGC GCC AGT CAG AGC AGC AAA
```

FIG. 4

His Asp Gln Asp Asp Arg Gly Gly Ser Gly Ala Lys Ser Pro Ala Val Leu Ala Ala Arg
                                                                                40
Ala Gln Val Phe Lys Ala Asn Pro Gln Met Val Arg Ser Ile Met Glu Gly Gly Gly Phe
                                                                                60
Gly Thr Glu Leu Ser Tyr Ala Val Ala Asn Ser Met Tyr Ser Arg Thr Asp Gln Asn Ala
                                                                                80
Ile Ala Asp Ala Arg Ala Lys Leu Lys Val Glu Ala Val Ala Pro Arg Thr Trp Leu Leu
                                                                                100
Arg Phe Pro Ile Val Asn Val Val Val Phe Glu Thr Asp Glu Gly Leu Val Leu Val Asp
                                                                                120
Ser Gly Tyr Ala Pro Ala Gly Pro Ala Leu Ala Glu Thr Leu Lys Lys Leu Ser Asn Lys
                                                                                140
Pro Leu His Thr Val Ile Leu Thr His Phe His Ala Asp His Ala Phe Gly Ala Trp Ala
                                                                                160
Leu Met Asp Gln Lys Pro His Val Val Thr Glu Gln Arg Phe Ile Ser Gln Met Glu Leu
                                                                                180
Asp Met Arg Ser Asn Gly Leu Ile Ala Arg Asn Asn Gln Gln Ser Val Ala Asp Val Pro
                                                                                200
Arg Thr Trp Ala Asp Ala Val Arg Pro Thr Gln Thr Phe Arg Asp Lys Thr Thr Leu Lys
                                                                                220
Ile Gly Gly Glu Asp Phe Val Leu Thr His Ala Arg Gly Glu Thr Glu Asp Gln Ile Trp
                                                                                240
Val Ala Val Pro Gly Arg Lys Ile Val Ala Ser Ala Asp Tyr Phe Gln Gly Phe Leu Pro
                                                                                260
Asn Ala Gly Asn Gly Lys Arg Arg Gln Arg Tyr Pro Glu Glu Trp Ala Arg Ala Leu Arg
                                                                                280
Asp Met Ala Ala Leu Lys Pro Glu Leu Leu Leu Pro Ala His Gly Pro Ala Ile Thr Lys
                                                                                300
Pro Glu Glu Ile Gln Asp Arg Leu Pro Ala Gln Ala Gln Met Leu Asp Ser Ile Ser Arg
                                                                                320
Gln Val Val Ala Gly Leu Asn Ser Gly Val Arg Arg Asp Gln Val Ile Glu Lys Val Ala
                                                                                340
Leu Pro Pro Glu Leu Ala Arg Arg Ser Asp Ala Arg Glu Leu Tyr Val Ser Ala Lys Asp
                                                                                360
Ile Gly Arg Met Val Val Ser Glu Tyr Ser Gly Trp Trp Asp Asp Ile Pro Ser His Trp
                                                                                380
Arg Pro Ala Ser Leu Ala Asn Glu Ala Lys Glu Ile Val Gln Leu Ala Gly Gly Ala Arg
                                                                                400
Pro Val Ile Gln Arg Ala Val Ala Leu Ala Asp Ser Asn Pro Glu Leu Ala Ser His Leu
                                                                                420
Ala Asp Trp Ala Trp Tyr Ala Asp Ser Asp Asp Thr Glu Val Ala Gln Gly Ala Leu Lys
                                                                                440
Val Tyr Ser Ala Arg Val Ala Lys Pro Leu Pro Thr Gln Glu Val Leu Val Tyr Ala Glu
                                                                                460
His Met Val Arg Leu Gln Leu Lys Leu Asn Glu Leu Asn Ser Thr Arg Ala Ala Ser Ala
                                        467
Ser Gln Ser Ser Lys Ala His

5,585,255

BILE ACID SULFATE SULFATASE GENE, PLASMID CONTAINING SAID GENE AND METHOD OF PRODUCING BILE ACID SULFATE SULFATASE

TECHNICAL FIELD

The present invention relates to bile acid sulfate sulfatase and a gene therefor, a plasmid containing the gene coding for said protein, a transformant capable of producing bile acid sulfate sulfatase, and a method of producing bile acid sulfate sulfatase.

BACKGROUND ART

The present inventor previously searched for an enzyme capable of efficiently hydrolyze 3α-sulfuric acid esters of sulfated bile acids for the purpose of enabling enzymatic assay of sulfated bile acids in blood or urine. As a result, it was found that the bacterial species *Pseudomonas testosteroni*, which belongs to the genus Pseuomonas, produces the desired enzyme, bile acid sulfate sulfatase. The bile acid sulfate sulfatase produced by said bacterial species is characterized in that it acts on 3α-sulfated bile acids, leading to the formation of 3β-hydroxy bile acids. Therefore, it was made possible to assay 3α-sulfated bile acids by oxidizing said 3β-hydroxy bile acids to 3-oxobile acids under the action of β-hydroxysteroid dehydrogenase in the presence of β-NAD, which is a coenzyme for said dehydrogenase, with simultaneous reduction of β-NAD to NADH, and assaying the thus-formed NADH by a per se known method (cf. Japanese Unexamined Patent Publication No. 02-145,183).

However, such a method of producing bile acid sulfate sulfatase as mentioned above has drawbacks. Thus, it is an indispensable condition that cholic acid or the like, which is expensive, should be added, as an inducer substrate, to the medium. Moreover, the yield of bile acid sulfate sulfatase is low and the production procedure is rather complicated.

Accordingly, it is an object of the present invention to provide a method of producing 3α-bile acid sulfate sulfatase in high yields and at a low cost in an easy and simple manner.

BRIEF DESCRIPTION OF THE DRAWINGS

FIG. 3 shows the complete base sequence of the bile acid sulfate sulfatase gene (SEQ ID NO:1).

FIG. 4 shows the amino acid sequence of the peptide obtained by translation of the bile acid sulfate sulfatase gene (SEQ ID NO:2).

DISCLOSURE OF THE INVENTION

Figure 1:
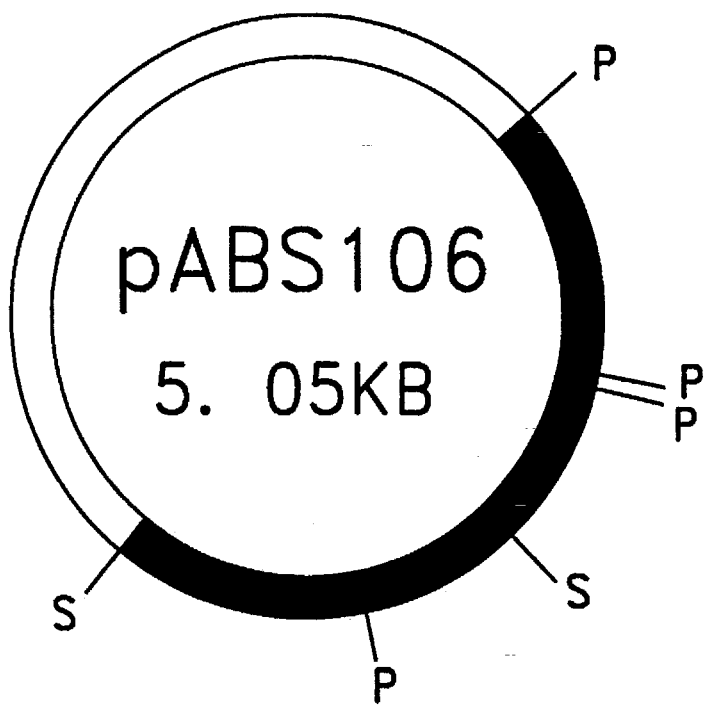
FIG. 1 shows a restriction enzyme map of a recombinant plasmid named pABS106.
Figure 1:
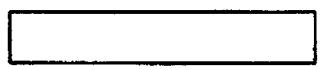
Figure 1:

The present inventor found that when a transformant (e.g. *Escherichia coli*) obtained by introduction of a recombinant DNA constructed by inserting, into a vector DNA (e.g. plasmid vector), a 2.36 kb DNA fragment containing the bile acid sulfate sulfatase gene region (1,509 bp) derived from a bile acid sulfate sulfatase-producing bacterial strain belonging to *Pseudomonas testosteroni*, for example *Pseudomonas testosteroni* ATCC 11996, is reared and cultivated in an ordinary nutrient medium, said enzyme can be produced efficiently in said transformant without adding any expensive substance such as mentioned above to the medium. The present invention has been completed based on this and other findings.

Thus, the present invention provides a bile acid sulfate sulfatase gene derived from bacteria belonging to *Pseudomonas testosteroni* and containing a DNA sequence coding for an amino acid sequence of the following formula (A) (SEQ ID NO:2):

```
                                                                            20   (A)
His Asp Gln Asp Asp Arg Gly Gly Ser Gly Ala Lys Ser Pro Ala Val Leu Ala Ala Arg
                                                                            40
Ala Gln Val Phe Lys Ala Asn Pro Gln Met Val Arg Ser Ile Met Glu Gly Gly Gly Phe
                                                                            60
Gly Thr Glu Leu Ser Tyr Ala Val Ala Asn Ser Met Tyr Ser Arg Thr Asp Gln Asn Ala
                                                                            80
Ile Ala Asp Ala Arg Ala Lys Leu Lys Val Glu Ala Val Ala Pro Arg Thr Trp Leu Leu
                                                                            100
Arg Phe Pro Ile Val Asn Val Val Phe Glu Thr Asp Glu Gly Leu Val Leu Val Asp
                                                                            120
Ser Gly Tyr Ala Pro Ala Gly Pro Ala Leu Ala Glu Thr Leu Lys Lys Leu Ser Asn Lys
                                                                            140
Pro Leu His Thr Val Ile Leu Thr His Phe His Ala Asp His Ala Phe Gly Ala Trp Ala
                                                                            160
Leu Met Asp Gln Lys Pro His Val Val Thr Glu Gln Arg Phe Ile Ser Gln Met Glu Leu
                                                                            180
Asp Met Arg Ser Asn Gly Leu Ile Ala Arg Asn Asn Gln Gln Ser Val Ala Asp Val Pro
                                                                            200
Arg Thr Trp Ala Asp Ala Val Arg Pro Thr Gln Thr Phe Arg Asp Lys Thr Thr Leu Lys
                                                                            220
Ile Gly Gly Glu Asp Phe Val Leu Thr His Ala Arg Gly Glu Thr Glu Asp Gln Ile Trp
                                                                            240
Val Ala Val Pro Gly Arg Lys Ile Val Ala Ser Ala Asp Tyr Phe Gln Gly Phe Leu Pro
```

```
                                                                          260
Asn Ala Gly Asn Gly Lys Arg Arg Gln Arg Tyr Pro Glu Glu Trp Ala Arg Ala Leu Arg

280
Asp Met Ala Ala Leu Lys Pro Glu Leu Leu Leu Pro Ala His Gly Pro Ala Ile Thr Lys

300
Pro Glu Glu Ile Gln Asp Arg Leu Pro Ala Gln Ala Gln Met Leu Asp Ser Ile Ser Arg

320
Gln Val Val Ala Gly Leu Asn Ser Gly Val Arg Arg Asp Gln Val Ile Glu Lys Val Ala

340
Leu Pro Pro Glu Leu Ala Arg Arg Ser Asp Ala Arg Glu Leu Tyr Val Ser Ala Lys Asp

360
Ile Gly Arg Met Val Val Ser Glu Tyr Ser Gly Trp Trp Asp Asp Ile Pro Ser His Trp

380
Arg Pro Ala Ser Leu Ala Asn Glu Ala Lys Glu Ile Val Gln Leu Ala Gly Gly Ala Arg

400
Pro Val Ile Gln Arg Ala Val Ala Leu Ala Asp Ser Asn Pro Glu Leu Ala Ser His Leu

420
Ala Asp Trp Ala Trp Tyr Ala Asp Ser Asp Asp Thr Glu Val Ala Gln Gly Ala Leu Lys

440
Val Tyr Ser Ala Arg Val Ala Lys Pro Leu Pro Thr Gln Glu Val Leu Val Tyr Ala Glu

460
His Met Val Arg Leu Gln Leu Lys Leu Asn Glu Leu Asn Ser Thr Arg Ala Ala Ser Ala

467
Ser Gln Ser Ser Lys Ala His
```

The invention also provides a bile acid sulfate sulfatase gene containing a DNA sequence of the following formula (B) (SEQ ID NO:1):

```
                        30                                                            60  (B)
ATG AAT GGA GCA ATG GCA AAC ATG AGA AAA GTA TCT CGC CTC TCC CGA TAC GCC TTT GCC 90                                                           120
ACA GCC CTG GCA CTG AGC CAG TTC GGC ACA GGC ACG GCC AAC GCC CAC GAT CAG GAT GAT 150                                                           180
CGC GGT GGC TCG GGA GCG AAA AGC CCC GCT GTG CTT GCT GCC CGC GCC CAG GTG TTC AAG 210                                                           240
GCC AAT CCG CAG ATG GTC AGG TCC ATC ATG GAA GGC GGT GGC TTT GGC ACC GAG CTG TCG 270                                                           300
TAT GCA GTA GCC AAC AGC ATG TAC AGC CGA ACC GAC CAG AAC GCC ATT GCA GAT GCC CGA 330                                                           360
GCC AAG CTC AAA GTC GAG GCC GTG GCT CCA CGC ACC TGG CTG CTG CGT TTC CCC ATC GTC 390                                                           420
AAC GTG GTG GTC TTC GAG ACC GAC GAA GGC CTG GTC TTG GTC GAT AGC GGC TAC GCA CCT 450                                                           480
GCA GGC CCG GCC TTG GCC GAA ACG CTG AAG AAG CTC AGC AAC AAG CCG TTG CAC ACC GTC 510                                                           540
ATC CTC ACG CAC TTT CAT GCC GAC CAT GCC TTT GGC GCC TGG GCG TTG ATG GAC CAG AAG 570                                                           600
CCG CAT GTA GTG ACC GAG CAG CGC TTC ATC TCC CAG ATG GAG CTG GAC ATG CGC AGC AAC 630                                                           660
GGT CTG ATT GCA CGC AAC AAC CAG CAA AGC GTG GCC GAT GTG CCC CGG ACC TGG GCA GAT 690                                                           720
GCA GTT CGG CCC ACC CAG ACC TTC AGG GAC AAG ACC ACA CTC AAA ATT GGC GGC GAA GAC 750                                                           780
TTT GTG CTG ACC CAT GCG CGC GGC GAG ACC GAA GAC CAG ATA TGG GTT GCC GTT CCA GGC
```

-continued

```
                                    810                                      840
CGG AAA ATC GTG GCC AGC GCG GAT TAT TTC CAG GGG TTT CTG CCC AAT GCG GGC AAC GGC
                                    870                                      900
AAG CGC CGC CAG CGC TAC CCC GAG GAG TGG GCC CGG GCC CTG CGC GAC ATG GCA GCA CTC
                                    930                                      960
AAA CCC GAG CTG CTG CTG CCG GCG CAT GGT CCG GCC ATC ACC AAG CCC GAG GAA ATT CAG
                                    990                                     1020
GAC CGA CTG CCC GCC CAG GCC CAG ATG CTG GAC AGC ATC TCC AGG CAA GTG GTG GCC GGC
                                   1050                                     1080
CTG AAC AGC GGA GTA CGC CGC GAT CAG GTC ATT GAA AAA GTC GCA CTG CCG CCG GAG CTG
                                   1110                                     1140
GCC CGG CGA AGC GAT GCA CGC GAG CTA TAT GTG TCT GCC AAA GAC ATA GGC CGC ATG GTG
                                   1170                                     1200
GTC AGC GAG TAC AGC GGC TGG TGG GAC GAT ATT CCA TCG CAC TGG CGC CCG GCG TCC CTG
                                   1230                                     1260
GCC AAT GAG GCC AAA GAA ATC GTG CAG CTA GCT GGC GGT GCC AGG CCG GTG ATT CAG CGT
                                   1290                                     1320
GCA GTG GCG CTG GCA GAC AGC AAT CCG GAG CTG GCC TCC CAT CTG GCC GAC TGG GCC TGG
                                   1350                                     1380
TAT GCA GAC AGC GAT GAC ACC GAG GTG GCT CAA GGC GCA CTG AAG GTC TAT TCC GCG CGT
                                   1410                                     1440
GTT GCC AAG CCT CTG CCC ACG CAG GAA GTG CTG GTC TAT GCC GAG CAC ATG GTG CGC CTG
                                   1470                                     1500
CAG CTC AAG CTC AAT GAG CTG AAC AGC ACA CGC GCG GCC AGC GCC AGT CAG AGC AGC AAA

GCG CAT TAA
```

The invention further provides a plasmid containing a DNA sequence coding for the amino acid sequence of the above formula (A) as derived from bacteria belonging to *Pseudomonas testosteroni*.

Still further, the invention provides bacteria belonging to *Escherichia coli* and harboring a plasmid containing a DNA sequence coding for the amino acid sequence shown by the above formula (A) as derived from bacteria belonging to *Pseudomonas testosteroni*.

Furthermore, the invention provides a method of producing bile acid sulfate sulfatase which comprises cultivating in a medium bacteria belonging to the genus Escherichia that have acquired the ability to produce bile acid sulfate sulfatase as a result of introduction thereinto of a novel recombinant DNA constructed by insertion of a DNA fragment derived from a bacterial strain belonging to *Pseudomonas testosteroni* and containing the bile acid sulfate sulfatase gene defined by the restriction enzyme map shown in FIG. 1 and recovering bile acid sulfate sulfatase from the culture.

The invention further provides a method of producing bile acid sulfate sulfatase as mentioned above in which the bile acid sulfate sulfatase gene contains a DNA sequence coding for an amino acid sequence of the following formula (A) (SEQ ID NO:2):

```
                                                                           20  (A)
        His Asp Gln Asp Asp Arg Gly Gly Ser Gly Ala Lys Ser Pro Ala Val Leu Ala Ala Arg
                                                                           40
        Ala Gln Val Phe Lys Ala Asn Pro Gln Met Val Arg Ser Ile Met Glu Gly Gly Gly Phe
                                                                           60
        Gly Thr Glu Leu Ser Tyr Ala Val Ala Asn Ser Met Tyr Ser Arg Thr Asp Gln Asn Ala
                                                                           80
        Ile Ala Asp Ala Arg Ala Lys Leu Lys Val Glu Ala Val Ala Pro Arg Thr Trp Leu Leu
                                                                          100
        Arg Phe Pro Ile Val Asn Val Val Phe Glu Thr Asp Glu Gly Leu Val Leu Val Asp
                                                                          120
        Ser Gly Tyr Ala Pro Ala Gly Pro Ala Leu Ala Glu Thr Leu Lys Lys Leu Ser Asn Lys
                                                                          140
        Pro Leu His Thr Val Ile Leu Thr His Phe His Ala Asp His Ala Phe Gly Ala Trp Ala
                                                                          160
        Leu Met Asp Gln Lys Pro His Val Val Thr Glu Gln Arg Phe Ile Ser Gln Met Glu Leu
                                                                          180
        Asp Met Arg Ser Asn Gly Leu Ile Ala Arg Asn Asn Gln Gln Ser Val Ala Asp Val Pro
```

```
                                                                          200
Arg Thr Trp Ala Asp Ala Val Arg Pro Thr Gln Thr Phe Arg Asp Lys Thr Thr Leu Lys
                                                                          220
Ile Gly Gly Glu Asp Phe Val Leu Thr His Ala Arg Gly Glu Thr Glu Asp Gln Ile Trp
                                                                          240
Val Ala Val Pro Gly Arg Lys Ile Val Ala Ser Ala Asp Tyr Phe Gln Gly Phe Leu Pro
                                                                          260
Asn Ala Gly Asn Gly Lys Arg Arg Gln Arg Tyr Pro Glu Glu Trp Ala Arg Ala Leu Arg
                                                                          280
Asp Met Ala Ala Leu Lys Pro Glu Leu Leu Pro Ala His Gly Pro Ala Ile Thr Lys
                                                                          300
Pro Glu Glu Ile Gln Asp Arg Leu Pro Ala Gln Ala Gln Met Leu Asp Ser Ile Ser Arg
                                                                          320
Gln Val Val Ala Gly Leu Asn Ser Gly Val Arg Arg Asp Gln Val Ile Glu Lys Val Ala
                                                                          340
Leu Pro Pro Glu Leu Ala Arg Arg Ser Asp Ala Arg Glu Leu Tyr Val Ser Ala Lys Asp
                                                                          360
Ile Gly Arg Met Val Val Ser Glu Tyr Ser Gly Trp Trp Asp Asp Ile Pro Ser His Trp
                                                                          380
Arg Pro Ala Ser Leu Ala Asn Glu Ala Lys Glu Ile Val Gln Leu Ala Gly Gly Ala Arg
                                                                          400
Pro Val Ile Gln Arg Ala Val Ala Leu Ala Asp Ser Asn Pro Glu Leu Ala Ser His Leu
                                                                          420
Ala Asp Trp Ala Trp Tyr Ala Asp Ser Asp Asp Thr Glu Val Ala Gln Gly Ala Leu Lys
                                                                          440
Val Tyr Ser Ala Arg Val Ala Lys Pro Leu Pro Thr Gln Glu Val Leu Val Tyr Ala Glu
                                                                          460
His Met Val Arg Leu Gln Leu Lys Leu Asn Glu Leu Asn Ser Thr Arg Ala Ala Ser Ala
                       467
Ser Gln Ser Ser Lys Ala His
```

The invention still further provides bile acid sulfate sulfatase containing an amino acid sequence of the following formula (A) (SEQ ID NO:2):

```
                                                                          20    (A)
His Asp Gln Asp Asp Arg Gly Gly Ser Gly Ala Lys Ser Pro Ala Val Leu Ala Ala Arg
                                                                          40
Ala Gln Val Phe Lys Ala Asn Pro Gln Met Val Arg Ser Ile Met Glu Gly Gly Gly Phe
                                                                          60
Gly Thr Glu Leu Ser Tyr Ala Val Ala Asn Ser Met Tyr Ser Arg Thr Asp Gln Asn Ala
                                                                          80
Ile Ala Asp Ala Arg Ala Lys Leu Lys Val Glu Ala Val Ala Pro Arg Thr Trp Leu Leu
                                                                          100
Arg Phe Pro Ile Val Asn Val Val Phe Glu Thr Asp Gly Leu Val Leu Val Asp
                                                                          120
Ser Gly Tyr Ala Pro Ala Gly Pro Ala Leu Ala Glu Thr Leu Lys Lys Leu Ser Asn Lys
                                                                          140
Pro Leu His Thr Val Ile Leu Thr His Phe His Ala Asp His Ala Phe Gly Ala Trp Ala
                                                                          160
Leu Met Asp Gln Lys Pro His Val Val Thr Glu Gln Arg Phe Ile Ser Gln Met Glu Leu
                                                                          180
Asp Met Arg Ser Asn Gly Leu Ile Ala Arg Asn Asn Gln Gln Ser Val Ala Asp Val Pro
                                                                          200
Arg Thr Trp Ala Asp Ala Val Arg Pro Thr Gln Thr Phe Arg Asp Lys Thr Thr Leu Lys
```

220
Ile Gly Gly Glu Asp Phe Val Leu Thr His Ala Arg Gly Glu Thr Glu Asp Gln Ile Trp

240
Val Ala Val Pro Gly Arg Lys Ile Val Ala Ser Ala Asp Tyr Phe Gln Gly Phe Leu Pro

260
Asn Ala Gly Asn Gly Lys Arg Arg Gln Arg Tyr Pro Glu Glu Trp Ala Arg Ala Leu Arg

280
Asp Met Ala Ala Leu Lys Pro Glu Leu Leu Leu Pro Ala His Gly Pro Ala Ile Thr Lys

300
Pro Glu Glu Ile Gln Asp Arg Leu Pro Ala Gln Ala Gln Met Leu Asp Ser Ile Ser Arg

320
Gln Val Val Ala Gly Leu Asn Ser Gly Val Arg Arg Asp Gln Val Ile Glu Lys Val Ala

340
Leu Pro Pro Glu Leu Ala Arg Arg Ser Asp Ala Arg Glu Leu Tyr Val Ser Ala Lys Asp

360
Ile Gly Arg Met Val Val Ser Glu Tyr Ser Gly Trp Trp Asp Asp Ile Pro Ser His Trp

380
Arg Pro Ala Ser Leu Ala Asn Glu Ala Lys Glu Ile Val Gln Leu Ala Gly Gly Ala Arg

400
Pro Val Ile Gln Arg Ala Val Ala Leu Ala Asp Ser Asn Pro Glu Leu Ala Ser His Leu

420
Ala Asp Trp Ala Trp Tyr Ala Asp Ser Asp Asp Thr Glu Val Ala Gln Gly Ala Leu Lys

440
Val Tyr Ser Ala Arg Val Ala Lys Pro Leu Pro Thr Gln Glu Val Leu Val Tyr Ala Glu

460
His Met Val Arg Leu Gln Leu Lys Leu Asn Glu Leu Asn Ser Thr Arg Ala Ala Ser Ala

467
Ser Gln Ser Ser Lys Ala His

In the following, the invention is illustrated in more detail.

First, as the bacterial strain belonging to *Pseudomonas testosteroni* and to serve as a bile acid sulfate sulfatase donor in the practice of the invention, there may be mentioned, for example, *Pseudomonas testosteroni* ATCC 11996 etc. Such bacterial strain is cultivated to give a culture. As the method of cultivation, there may be mentioned, for example, the method described in Japanese Unexamined Patent Publication No. 02-145,183 and the like. Specifically, cultivation is conducted in a medium for general bacteria, for example LB medium, generally under aerobic conditions, at about 24° to about 34° C. for about 12 to about 24 hours. From the culture obtained in that manner, cells are harvested by a conventional method, for example by filtration, centrifugation, etc. The chromosomal DNA can be obtained from the cells by the phenol method [Biochimica et Biophysica Acta, vol. 72, pp. 619–629 (1963)], for instance.

The thus-obtained chromosomal DNA is then inserted into a vector DNA. The method of insertion is not limited to any particular one. Thus, for example, the insertion can be effected by cleaving the chromosomal DNA and vector DNA using a variety of restriction enzymes for preparing DNA fragments and then mixing both DNA fragments together, followed by treatment with a DNA ligase. As the restriction enzymes, there may be mentioned, for example, BamHI, EcoRI, HindIII, PstI, SmaI, etc.

Then, the recombinant DNA obtained in the above manner is introduced into host cells, in particular cells of a bacterial strain belonging to the genus Escherichia, for example *Escherichia coli* JM109 or *Escherichia coli* HB101, by a conventional method, for example by the calcium chloride treatment method.

An *Escherichia coli* strain harboring the desired recombinant plasmid (with the bile acid sulfate sulfatase inserted therein) can be selected and isolated by allowing the disrupted cell extract to act on a sulfated bile acids, for example cholic acid 3-sulfate, and detecting the desulfation product isocholic acid (5β-cholanic acid-3β,7α,12α-triol) by thin layer chromatography (TLC).

Then, the recombinant plasmid with a bile acid sulfate sulfatase gene-containing DNA fragment inserted therein is extracted and purified from the strain obtained in the above manner and showing bile acid sulfate sulfatase activity by using the method described in Molecular Cloning, Second Edition, vol. 1, pages 21–24, for instance. Said recombinant plasmid is further subjected to subcloning according to a conventional procedure. In this manner, a novel recombinant plasmid with a 2.36 kb DNA fragment, which contains the bile acid sulfate sulfatase gene, inserted therein is obtained (cf. FIG. 1).

Using the above-mentioned bile acid sulfate sulfatase gene-containing recombinant plasmid, the complete base sequence of the bile acid sulfate sulfatase gene alone is analyzed (cf. FIG. 3) and, then, the amino acid sequence of the polypeptide actually obtained by translation of the gene having said base sequence is ascertained (cf. FIG. 4). As shown later in an example, the polypeptide obtainable is not the peptide resulting from faithful translation of FIG. 3, but a peptide beginning with His as resulting from deletion of 28 or more amino acid residues on the N-terminal side. This is the finding obtained for the first time in connection with the present invention.

For producing bile acid sulfate sulfatase using the *Escherichia coli* strain obtained as mentioned above and harboring the recombinant plasmid with the bile acid sulfate sulfatase gene-containing DNA fragment inserted therein, said *Escherichia coli* strain is cultivated in the following manner to give cultured cells.

Said *Escherichia coli* strain may be cultivated in the manner of ordinary solid culture but is preferably cultivated by a liquid culture method. The medium for cultivating said *Escherichia coli* strain may be any of those synthetic, semisynthetic or natural media containing carbon sources, nitrogen sources, inorganic compounds and other nutrients, and generally used for bacterial culture. As the carbon sources utilizable in the above media, there may be mentioned, for example, saccharide solutions containing glucose, fructose, invert sugar, saccharified starch, sorbitol, glycerol, etc., and organic acids such as pyruvic acid, malic acid, succinic acid etc. As the nitrogen sources, there may be mentioned, for example, ammonium sulfate, ammonium chloride, ammonium nitrate, ammonium phosphate, ammonium hydroxide, ammonium tartrate, ammonium acetate, urea and so forth. Peptone, yeast extract, meat extract, corn steep liquor and the like can be used not only as carbon sources but also as nitrogen sources. The inorganic compounds include monopotassium phosphate, dipotassium phosphate, monosodium phosphate, disodium phosphate, magnesium sulfate, magnesium chloride, potassium chloride, sodium chloride, ferrous sulfate, ferrous chloride, ferric sulfate, ferric chloride, manganese sulfate, manganese chloride, etc.

The cultivation period and cultivation temperature are not critical but are preferably within the range of 25° C. to 42° C., preferably around 30° C., and 6 to 24 hours, preferably 8 to 14 hours, respectively. Cultivation is carried out under these conditions in the manner of ordinary shaking culture or submerged culture (cultivation with aeration and agitation).

The enzyme in question is extracted from the cells obtained by the cultivation. The extraction can be carried out by a conventional method for extracting intracellular enzymes. Thus, for instance, the cells are disrupted by ultrasonic treatment, any of various mechanical treatments, or enzyme treatment, and the insoluble matter is removed by centrifugation, for instance, whereby the enzyme can be recovered in the supernatant. This crude enzyme can be purified by a combination of appropriate techniques selected from among those generally known for enzyme purification. Thus, for example, bile acid sulfate sulfatase can be obtained by treatment for nucleic acid removal, salting out with ammonium sulfate, ion exchange chromatography, gel filtration, etc.

In the gene of the present invention, the code for each amino acid may be alternative, hence said gene may be any of those coding for the amino acid sequence defined by formula (A). The amino acid sequence defined by formula (A) is a minimum requirement. Thus, the gene defined by formula (B) and the like genes longer than said sequence are also included within the scope of the present invention. The DNA sequences beginning with any of the three ATG codons numbered 1–3, (SEQ ID NO:1), 13–15 (SEQ ID NO:3) and 22–24 (SEQ ID NO:4) in the DNA sequence defined by formula (B) are also included within the scope of the present invention.

The gene of the invention, which encodes the amino acid sequence of formula (A), remains within the scope of the invention even when a plurality of amino acid residues on the N-terminal and/or C-terminal side are cleaved off by means of an exopeptidase, for example carboxypeptidase, in the range reserving the enzymatic activity.

The plasmid to be used as the vector DNA in the practice of the invention preferably contains an appropriate selective marker and is preferably amplifiable to a large copy number. As examples, there may be mentioned pUC18, pUC19, pBR322, pTrc99A, etc.

The method of the invention consists in isolating a DNA fragment containing the gene for bile acid sulfate sulfatase that *Pseudomonas testosteroni* produces, constructing a recombinant plasmid containing said DNA fragment, utilizing this to transform *Escherichia coli*, cultivating the transformant to thereby cause intracellular production of a large quantity of bile acid sulfate sulfatase, and recovering the same. The productivity of the genetically engineered strain obtained in accordance with the invention is about 100 times in the production of bile acid sulfate sulfatase as compared with the original strain and thus facilitates the production of the enzyme. The addition of an inducer substrate such as cholic acid, which is expensive, for inducing bile acid sulfate sulfatase is no longer necessary.

EXAMPLE

The following example is further illustrative of the present invention.

(1) Preparation of chromosomal DNA

*Pseudomonas testosteroni* ATCC 11996 having bile acid sulfate sulfatase activity was inoculated into 750 ml of LB medium (10 g/L tryptone, 5 g/L yeast extract, 10 g/L sodium chloride, pH 7.0), shaking culture was conducted at 30° C. for 12 hours and cells were then harvested by centrifugation. Chromosomal DNA was extracted from the thus-obtained cells by the phenol method [Biochimica et Biophysica Acta, vol. 72, pp. 619–629 (1963)]. About 5 mg of chromosomal DNA was thus obtained.

(2) Preparation of a recombinant plasmid by insertion of a chromosomal DNA fragment To 70 µg of the chromosomal DNA obtained in (1) was added the restriction enzyme EcoRI, and the DNA was partially digested by incubation at 37° C. for 30 minutes, 60 minutes or 90 minutes. The digests thus obtained were combined and subjected to electrophoresis using a low melting agarose gel, and DNA fragments with a size of 3 kb to 7 kb were recovered. These were purified by treatment with phenol, treatment with ether and precipitation with ethanol to give purified DNA fragments. Separately, the restriction enzyme EcoRI was added to 2 µg of the plasmid pUC18 employed as the vector, and the plasmid was completely cleaved by incubation at 37° C. for 2 hours. The subsequent purification by treatment with alkaline phosphatase, treatment with phenol, treatment with ether and precipitation with ethanol gave EcoRI-cleaved pUC18.

The thus-obtained plasmid pUC18 and the chromosomal DNA fragments mentioned above were respectively dissolved in a buffer solution and the solutions were combined. T4 DNA ligase was further added and the ligation reaction was carried out at 10° C. for 15 hours to give a recombinant plasmid solution.

(3) Transformation of *Escherichia coli* with recombinant plasmids

*Escherichia coli* JM109 was shake-cultured in 50 ml of LB medium at 37° C. for 2 hours, cells were collected by centrifugation and suspended in 50 ml of 100 mM magnesium chloride solution, and the suspension was maintained on ice for 5 minutes and then centrifuged. The cells thus recovered were further suspended in 50 ml of 100 mM calcium chloride solution, the suspension was maintained on ice for 1 hour and then centrifuged. The cells thus recovered were again suspended in 4 ml of 100 mM calcium chloride solution. To 0.4 ml of this cell suspension was added the recombinant plasmid solution prepared in (2). The mixture was allowed to stand on ice for 30 minutes and then heat-treated at 42° C. for 90 seconds for incorporation of the plasmid DNA into cells of said bacterial strain, i.e. for transformation. To the suspension of the thus-transformed cells was added 4 ml of LB medium, and shaking culture was performed at 37° C. for 1 hour. The culture was then spread onto an LB agar medium plate supplemented with 100 mg/L of ampicillin, 23.8 mg/L of IPTG (isopropyl 1-thio-β-D-galactoside) and 20 mg/L of X-Gal (5-bromo-4-chloro-3-indolyl β-D-galactoside) and cultured at 37° C. for 18 hours.

(4) Isolation of a transformant capable of producing bile acid sulfate sulfatase.

A white colony formed on the agar plate in (3) was shake-cultured in 5 ml of LB medium (containing 100 mg/L of ampicillin and 23.8 mg/L of IPTG) at 37° C. for 13 hours and, then, cells were separated by centrifugation. The cells were suspended in 0.5 ml of a buffer solution and disrupted by sonication. The subsequent centrifugation gave a bacterial cell extract. This cell extract was allowed to act on cholic acid 3-sulfate, the substrate of bile acid sulfate sulfatase, at 30° C. for at least 24 hours and isocholic acid, the reaction product, was detected by thin layer chromatography. Thus was obtained a transformant Escherichia coli strain capable of producing bile acid sulfate sulfatase.

Figure 2:
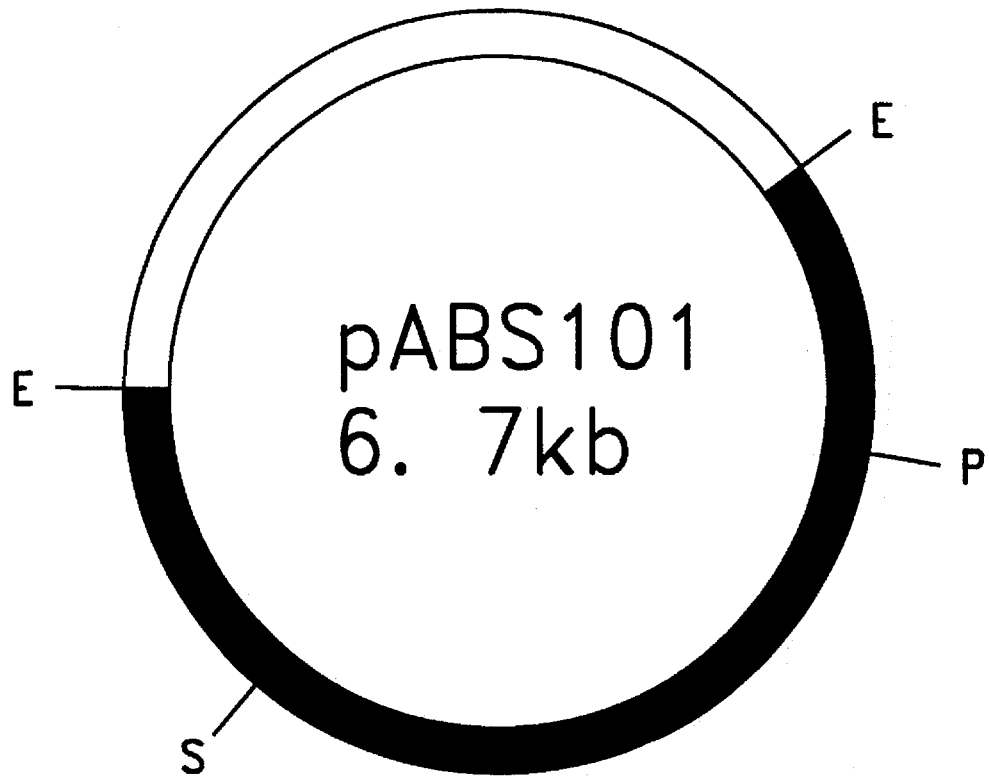
FIG. 2 shows a restriction enzyme map of a recombinant plasmid named pABS101.
Figure 2:
Figure 2:

The recombinant plasmid contained in this transformant Escherichia coli was named pABS101. A restriction enzyme map of said plasmid is shown in FIG. 2.

(5) Construction of a recombinant plasmid named pABS106

The DNA fragment inserted in pABS101 was subcloned. Thus, further cleavage was effected using PstI and SmaI, fragments were inserted into the plasmid pUC18, followed by introduction into Escherichia coli JM109 and further subjected to bile acid sulfate sulfatase activity assay. The bile acid sulfate sulfatase activity assay was performed by the method described in Japanese Unexamined Patent Publication No. 02-145,183. Thus, 0.1 ml of 2.5 mM aqueous solution of lithochloic acid sulfate (Sigma), 0.2 ml of 15 mM aqueous solution of β-NAD (Oriental Yeast), 1.0 ml of 0.1 mM Tris-hydrochloride buffer (pH 8.0) and 1.55 ml of distilled water were placed in a quartz cell and, after equilibrated at 30° C., 0.05 ml of a solution of β-hydroxysteroid dehydrogenase (Sigma) (10 U/ml) and 0.1 ml of each cell disruption product supernatant were added in that order and the enzyme reaction was started at 30° C. The increment in absorbance at 340 nm in the early reaction stage was measured. As a result, the existence of bile acid sulfate sulfatase activity was observed in a 2.36 kb DNA fragment inserted in the plasmid pABS106 shown in FIG. 1. The Escherichia coli strain harboring said plasmid introduced therein was named Escherichia coli JM109/pABS106 and had been deposited with the Fermentation Research Institute of the Agency of Industrial Science and Technology under the designation Escherichia coli JM109/pABS106 and the accession number FERM-3715.

(6) Production of bile acid sulfate sulfatase

Using Escherichia coli JM109 transformed by introduction of the bile acid sulfate sulfatase gene-containing plasmid pABS106 mentioned above, bile acid sulfate sulfatase was produced. One liter of a medium (containing 100 mg/L ampicillin; pH 6.0) comprising 2% yeast extract, 1% succinic acid and 0.01% manganese chloride was distributed, in 200-ml portions, into 2-liter flasks for shaking culture, the above strain was inoculated into each portion of the medium, and shaking culture was performed. About 8 hours after initiation of the cultivation, IPTG was added to 0.1 mM, and shaking culture was further continued for 4 hours. Cells were then harvested by centrifugation and suspended in 30 mM phosphate buffer (pH 7.2). The cells were disrupted using a sonic oscillator and the precipitate was removed by centrifugation to give a crude enzyme solution. This crude enzyme solution was deprived of nucleic acids using protamine sulfate and then subjected to salting-out treatment using ammonium sulfate. The precipitate fractions resulting from 33 to 70% saturation with ammonium sulfate were collected and dialyzed against 10 mM phosphate buffer (pH 7.2). The dialyzate was passed through a DEAE-cellulose (Whatman) column equilibrated with 10 mM phosphate buffer (pH 7.2). The unadsorbed fraction obtained was concentrated by salting out treatment with ammonium sulfate and then passed through a DEAE-Sepharose (Pharmacia) column equilibrated with 5 mM Tris-hydrochloride buffer (pH 8.0) containing 0.5 mM $MnCl_2$. The unadsorbed fraction obtained was concentrated by salting out treatment with ammonium sulfate and thereafter subjected to gel filtration by passing through a Sephacryl S-200 (Pharmacia) column equilibrated with 50 mM phosphate buffer (pH 6.8) containing 0.15 M NaCl and 0.5 mM $MnCl_2$. The active fraction was desalted by dialysis and obtained 500 units of bile acid sulfate sulfatase.

The enzyme activity was measured by the above-mentioned method comprising reacting the enzyme with lithocholic acid sulfate in the presence of β-NAD and β-hydroxysteroid dehydrogenase at 30° C. and measuring the increment in absorbance at 340 nm in the early stage of reaction. Each unit was defined as the quantity of enzyme forming 1 μmol of NADH in one minute. Finally, the productivity of bile acid sulfate sulfatase using the recombinant Escherichia coli JM109 became about 100 times higher as compared with Pseudomonas testosteroni.

(7) Analysis of the base sequence of the bile acid sulfate sulfatase gene-containing DNA The base sequence of the recombinant plasmid pABS106 was analyzed by the dideoxy method. For gel electrophoresis for the analysis, a 6% polyacrylamide gel was used.

The thus-obtained complete base sequence of the bile acid sulfate sulfatase gene portion alone is shown in FIG. 3, and the amino acid sequence of the polypeptide obtained as a result of translation of said gene is shown in FIG. 4.

We claim:

1. An isolated polynucleotide sequence coding for a bile acid sulfate sulfatase, which has the polynucleotide sequence of SEQ ID NO:1.

2. An isolated polynucleotide sequence coding for a bile acid sulfate sulfatase, which has the polynucleotide sequence of SEQ ID NO:3.

3. An isolated polynucleotide sequence coding for a bile acid sulfate sulfatase, which has the polynucleotide sequence of SEQ ID NO:4.

4. A plasmid containing the polynucleotide sequence selected from the group consisting of SEQ ID NOs: 1, 3 and 4.

5. A method for producing bile acid sulfate sulfatase which comprises the steps of:

a. extracting chromosomal DNA from a *Pseudomonas testosteroni* strain having bile acid sulfate sulfatase activity;

b. digesting said chromosomal DNA with the restriction enzymes PstI and SmaI to obtain at least a DNA fragment having a size of 2.36 kb;

c. inserting said DNA fragment into a vector DNA to obtain a recombinant DNA;

d. transforming an *Escherichia coli* strain with said recombinant DNA;

e. screening a transformant harboring said recombinant DNA containing said DNA fragment of 2.36 kb by assaying the bile acid sulfate sulfatase activity;

f. cultivating said transformant in a culture medium to produce bile acid sulfate sulfatase; and g. recovering bile acid sulfate sulfatase from the culture.

6. The method for producing bile acid sulfate sulfatase according to claim 5, wherein step (b) comprises the steps of:

i. digesting said chromosomal DNA with the restriction enzyme EcoRI so as to recover DNA fragments having a size of 3 kb to 7 kb;

ii. inserting said DNA fragments into vector DNAs to obtain a recombinant DNA;

iii. transforming an *Escherichia coli* strain with said recombinant DNA obtained to obtain a transformant producing bile acid sulfate sulfatase; and iv. subcloning said DNA fragment in said recombinant DNA contained in said transformant by cleaving the DNA fragment with the restriction enzymes PstI and SmaI, followed by inserting the cleaved fragment into a vector DNA to obtain a recombinant DNA.

7. The method for producing bile acid sulfate sulfatase according to claim 5, wherein said DNA fragment in step (b) comprises a polynucleotide coding for a peptide having the amino acid sequence of SEQ ID NO:2.

8. The method for producing bile acid sulfate sulfatase according to claim 7, wherein said DNA fragment comprises a polynucleotide having the sequence selected from the group consisting of SEQ ID NOs: 1, 3 and 4.

9. The method for producing bile acid sulfate sulfatase according to claim 5, wherein said vector DNA in step (c) is the plasmid pUC18.

10. The method for producing bile acid sulfate sulfatase according to claim 5, wherein said *Escherichia coli* strain in step (d) is *Escherichia coli* JM109.

11. The method for producing bile acid sulfate sulfatase according to claim 5, wherein said screened transformant in step (e) is a transformed *Escherichia coli* with the accession number FERM BP-3715.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 1509 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i i ) IMMEDIATE SOURCE:
    ( B ) CLONE: BILE ACID SULFATASE ( i x ) FEATURE:
    ( A ) NAME/KEY: CDS
    ( B ) LOCATION: 106..1509

( x i ) SEQUENCE DESCRIPTION: SEQ ID NO:1:

```
ATGAATGGAG CAATGGCAAA CATGAGAAAA GTATCTCGCC TCTCCCGATA CGCCTTTGCC         60

ACAGCCCTGG CACTGAGCCA GTTCGGCACA GGCACGGCCA ACGCC CAC GAT CAG           114
                                                  His Asp Gln
                                                    1

GAT GAT CGC GGT GGC TCG GGA GCG AAA AGC CCC GCT GTG CTT GCT GCC          162
Asp Asp Arg Gly Gly Ser Gly Ala Lys Ser Pro Ala Val Leu Ala Ala
        5               10                  15

CGC GCC CAG GTG TTC AAG GCC AAT CCG CAG ATG GTC AGG TCC ATC ATG          210
Arg Ala Gln Val Phe Lys Ala Asn Pro Gln Met Val Arg Ser Ile Met
 20              25                  30                      35

GAA GGC GGT GGC TTT GGC ACC GAG CTG TCG TAT GCA GTA GCC AAC AGC          258
Glu Gly Gly Gly Phe Gly Thr Glu Leu Ser Tyr Ala Val Ala Asn Ser
                 40                  45                  50

ATG TAC AGC CGA ACC GAC CAG AAC GCC ATT GCA GAT GCC CGA GCC AAG          306
Met Tyr Ser Arg Thr Asp Gln Asn Ala Ile Ala Asp Ala Arg Ala Lys
             55                  60                  65

CTC AAA GTC GAG GCC GTG GCT CCA CGC ACC TGG CTG CTG CGT TTC CCC          354
Leu Lys Val Glu Ala Val Ala Pro Arg Thr Trp Leu Leu Arg Phe Pro
         70                  75                  80

ATC GTC AAC GTG GTG GTC TTC GAG ACC GAC GAA GGC CTG GTC TTG GTC          402
Ile Val Asn Val Val Val Phe Glu Thr Asp Glu Gly Leu Val Leu Val
     85                  90                  95

GAT AGC GGC TAC GCA CCT GCA GGC CCG GCC TTG GCC GAA ACG CTG AAG          450
Asp Ser Gly Tyr Ala Pro Ala Gly Pro Ala Leu Ala Glu Thr Leu Lys
100             105                 110                 115

AAG CTC AGC AAC AAG CCG TTG CAC ACC GTC ATC CTC ACG CAC TTT CAT          498
Lys Leu Ser Asn Lys Pro Leu His Thr Val Ile Leu Thr His Phe His
                120                 125                 130

GCC GAC CAT GCC TTT GGC GCC TGG GCG TTG ATG GAC CAG AAG CCG CAT          546
Ala Asp His Ala Phe Gly Ala Trp Ala Leu Met Asp Gln Lys Pro His
            135                 140                 145

GTA GTG ACC GAG CAG CGC TTC ATC TCC CAG ATG GAG CTG GAC ATG CGC          594
Val Val Thr Glu Gln Arg Phe Ile Ser Gln Met Glu Leu Asp Met Arg
        150                 155                 160

AGC AAC GGT CTG ATT GCA CGC AAC AAC CAG CAA AGC GTG GCC GAT GTG          642
Ser Asn Gly Leu Ile Ala Arg Asn Asn Gln Gln Ser Val Ala Asp Val
    165                 170                 175

CCC CGG ACC TGG GCA GAT GCA GTT CGG CCC ACC CAG ACC TTC AGG GAC          690
Pro Arg Thr Trp Ala Asp Ala Val Arg Pro Thr Gln Thr Phe Arg Asp
180                 185                 190                 195

AAG ACC ACA CTC AAA ATT GGC GGC GAA GAC TTT GTG CTG ACC CAT GCG          738
Lys Thr Thr Leu Lys Ile Gly Gly Glu Asp Phe Val Leu Thr His Ala
                200                 205                 210

CGC GGC GAG ACC GAA GAC CAG ATA TGG GTT GCC GTT CCA GGC CGG AAA          786
Arg Gly Glu Thr Glu Asp Gln Ile Trp Val Ala Val Pro Gly Arg Lys
            215                 220                 225

ATC GTG GCC AGC GCG GAT TAT TTC CAG GGG TTT CTG CCC AAT GCG GGC          834
Ile Val Ala Ser Ala Asp Tyr Phe Gln Gly Phe Leu Pro Asn Ala Gly
        230                 235                 240
```

| | | | | | | | | | | | | | | | | |
|---|---|---|---|---|---|---|---|---|---|---|---|---|---|---|---|---|
| AAC | GGC | AAG | CGC | CGC | CAG | CGC | TAC | CCC | GAG | GAG | TGG | GCC | CGG | GCC | CTG | 882 |
| Asn | Gly | Lys | Arg | Arg | Gln | Arg | Tyr | Pro | Glu | Glu | Trp | Ala | Arg | Ala | Leu | |
| | 245 | | | | 250 | | | | | 255 | | | | | | |
| CGC | GAC | ATG | GCA | GCA | CTC | AAA | CCC | GAG | CTG | CTG | CTG | CCG | GCG | CAT | GGT | 930 |
| Arg | Asp | Met | Ala | Ala | Leu | Lys | Pro | Glu | Leu | Leu | Leu | Pro | Ala | His | Gly | |
| 260 | | | | | 265 | | | | | 270 | | | | | 275 | |
| CCG | GCC | ATC | ACC | AAG | CCC | GAG | GAA | ATT | CAG | GAC | CGA | CTG | CCC | GCC | CAG | 978 |
| Pro | Ala | Ile | Thr | Lys | Pro | Glu | Glu | Ile | Gln | Asp | Arg | Leu | Pro | Ala | Gln | |
| | | | | 280 | | | | | 285 | | | | | 290 | | |
| GCC | CAG | ATG | CTG | GAC | AGC | ATC | TCC | AGG | CAA | GTG | GTG | GCC | GGC | CTG | AAC | 1026 |
| Ala | Gln | Met | Leu | Asp | Ser | Ile | Ser | Arg | Gln | Val | Val | Ala | Gly | Leu | Asn | |
| | | | 295 | | | | | 300 | | | | | 305 | | | |
| AGC | GGA | GTA | CGC | CGC | GAT | CAG | GTC | ATT | GAA | AAA | GTC | GCA | CTG | CCG | CCG | 1074 |
| Ser | Gly | Val | Arg | Arg | Asp | Gln | Val | Ile | Glu | Lys | Val | Ala | Leu | Pro | Pro | |
| | | 310 | | | | | 315 | | | | 320 | | | | | |
| GAG | CTG | GCC | CGG | CGA | AGC | GAT | GCA | CGC | GAG | CTA | TAT | GTG | TCT | GCC | AAA | 1122 |
| Glu | Leu | Ala | Arg | Arg | Ser | Asp | Ala | Arg | Glu | Leu | Tyr | Val | Ser | Ala | Lys | |
| | 325 | | | | | 330 | | | | | 335 | | | | | |
| GAC | ATA | GGC | CGC | ATG | GTG | GTC | AGC | GAG | TAC | AGC | GGC | TGG | TGG | GAC | GAT | 1170 |
| Asp | Ile | Gly | Arg | Met | Val | Val | Ser | Glu | Tyr | Ser | Gly | Trp | Trp | Asp | Asp | |
| 340 | | | | | 345 | | | | | 350 | | | | | 355 | |
| ATT | CCA | TCG | CAC | TGG | CGC | CCG | GCG | TCC | CTG | GCC | AAT | GAG | GCC | AAA | GAA | 1218 |
| Ile | Pro | Ser | His | Trp | Arg | Pro | Ala | Ser | Leu | Ala | Asn | Glu | Ala | Lys | Glu | |
| | | | | 360 | | | | | 365 | | | | | 370 | | |
| ATC | GTG | CAG | CTA | GCT | GGC | GGT | GCC | AGG | CCG | GTG | ATT | CAG | CGT | GCA | GTG | 1266 |
| Ile | Val | Gln | Leu | Ala | Gly | Gly | Ala | Arg | Pro | Val | Ile | Gln | Arg | Ala | Val | |
| | | | 375 | | | | | 380 | | | | | 385 | | | |
| GCG | CTG | GCA | GAC | AGC | AAT | CCG | GAG | CTG | GCC | TCC | CAT | CTG | GCC | GAC | TGG | 1314 |
| Ala | Leu | Ala | Asp | Ser | Asn | Pro | Glu | Leu | Ala | Ser | His | Leu | Ala | Asp | Trp | |
| | | 390 | | | | | 395 | | | | | 400 | | | | |
| GCC | TGG | TAT | GCA | GAC | AGC | GAT | GAC | ACC | GAG | GTG | GCT | CAA | GGC | GCA | CTG | 1362 |
| Ala | Trp | Tyr | Ala | Asp | Ser | Asp | Asp | Thr | Glu | Val | Ala | Gln | Gly | Ala | Leu | |
| | 405 | | | | | 410 | | | | | 415 | | | | | |
| AAG | GTC | TAT | TCC | GCG | CGT | GTT | GCC | AAG | CCT | CTG | CCC | ACG | CAG | GAA | GTG | 1410 |
| Lys | Val | Tyr | Ser | Ala | Arg | Val | Ala | Lys | Pro | Leu | Pro | Thr | Gln | Glu | Val | |
| 420 | | | | | 425 | | | | | 430 | | | | | 435 | |
| CTG | GTC | TAT | GCC | GAG | CAC | ATG | GTG | CGC | CTG | CAG | CTC | AAG | CTC | AAT | GAG | 1458 |
| Leu | Val | Tyr | Ala | Glu | His | Met | Val | Arg | Leu | Gln | Leu | Lys | Leu | Asn | Glu | |
| | | | | 440 | | | | | 445 | | | | | 450 | | |
| CTG | AAC | AGC | ACA | CGC | GCG | GCC | AGC | GCC | AGT | CAG | AGC | AGC | AAA | GCG | CAT | 1506 |
| Leu | Asn | Ser | Thr | Arg | Ala | Ala | Ser | Ala | Ser | Gln | Ser | Ser | Lys | Ala | His | |
| | | | 455 | | | | | 460 | | | | | 465 | | | |
| TAA | | | | | | | | | | | | | | | | 1509 |

( 2 ) INFORMATION FOR SEQ ID NO:2:

( i ) SEQUENCE CHARACTERISTICS:
        ( A ) LENGTH: 467 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| His | Asp | Gln | Asp | Asp | Arg | Gly | Gly | Ser | Gly | Ala | Lys | Ser | Pro | Ala | Val |
| 1 | | | | 5 | | | | | 10 | | | | | 15 | |
| Leu | Ala | Ala | Arg | Ala | Gln | Val | Phe | Lys | Ala | Asn | Pro | Gln | Met | Val | Arg |
| | | | 20 | | | | | 25 | | | | | 30 | | |
| Ser | Ile | Met | Glu | Gly | Gly | Gly | Phe | Gly | Thr | Glu | Leu | Ser | Tyr | Ala | Val |
| | | 35 | | | | | 40 | | | | | 45 | | | |

```
Ala Asn Ser Met Tyr Ser Arg Thr Asp Gln Asn Ala Ile Ala Asp Ala
    50                  55                  60

Arg Ala Lys Leu Lys Val Glu Ala Val Ala Pro Arg Thr Trp Leu Leu
65                  70                  75                  80

Arg Phe Pro Ile Val Asn Val Val Val Phe Glu Thr Asp Glu Gly Leu
                85                  90                  95

Val Leu Val Asp Ser Gly Tyr Ala Pro Ala Gly Pro Ala Leu Ala Glu
            100                 105                 110

Thr Leu Lys Lys Leu Ser Asn Lys Pro Leu His Thr Val Ile Leu Thr
        115                 120                 125

His Phe His Ala Asp His Ala Phe Gly Ala Trp Ala Leu Met Asp Gln
    130                 135                 140

Lys Pro His Val Val Thr Glu Gln Arg Phe Ile Ser Gln Met Glu Leu
145                 150                 155                 160

Asp Met Arg Ser Asn Gly Leu Ile Ala Arg Asn Asn Gln Gln Ser Val
                165                 170                 175

Ala Asp Val Pro Arg Thr Trp Ala Asp Ala Val Arg Pro Thr Gln Thr
            180                 185                 190

Phe Arg Asp Lys Thr Thr Leu Lys Ile Gly Gly Glu Asp Phe Val Leu
        195                 200                 205

Thr His Ala Arg Gly Glu Thr Glu Asp Gln Ile Trp Val Ala Val Pro
    210                 215                 220

Gly Arg Lys Ile Val Ala Ser Ala Asp Tyr Phe Gln Gly Phe Leu Pro
225                 230                 235                 240

Asn Ala Gly Asn Gly Lys Arg Arg Gln Arg Tyr Pro Glu Glu Trp Ala
                245                 250                 255

Arg Ala Leu Arg Asp Met Ala Ala Leu Lys Pro Glu Leu Leu Leu Pro
            260                 265                 270

Ala His Gly Pro Ala Ile Thr Lys Pro Glu Glu Ile Gln Asp Arg Leu
        275                 280                 285

Pro Ala Gln Ala Gln Met Leu Asp Ser Ile Ser Arg Gln Val Val Ala
    290                 295                 300

Gly Leu Asn Ser Gly Val Arg Arg Asp Gln Val Ile Glu Lys Val Ala
305                 310                 315                 320

Leu Pro Pro Glu Leu Ala Arg Arg Ser Asp Ala Arg Glu Leu Tyr Val
                325                 330                 335

Ser Ala Lys Asp Ile Gly Arg Met Val Val Ser Glu Tyr Ser Gly Trp
            340                 345                 350

Trp Asp Asp Ile Pro Ser His Trp Arg Pro Ala Ser Leu Ala Asn Glu
        355                 360                 365

Ala Lys Glu Ile Val Gln Leu Ala Gly Gly Ala Arg Pro Val Ile Gln
    370                 375                 380

Arg Ala Val Ala Leu Ala Asp Ser Asn Pro Glu Leu Ala Ser His Leu
385                 390                 395                 400

Ala Asp Trp Ala Trp Tyr Ala Asp Ser Asp Asp Thr Glu Val Ala Gln
                405                 410                 415

Gly Ala Leu Lys Val Tyr Ser Ala Arg Val Ala Lys Pro Leu Pro Thr
            420                 425                 430

Gln Glu Val Leu Val Tyr Ala Glu His Met Val Arg Leu Gln Leu Lys
        435                 440                 445

Leu Asn Glu Leu Asn Ser Thr Arg Ala Ala Ser Ala Ser Gln Ser Ser
    450                 455                 460

Lys Ala His
465
```

( 2 ) INFORMATION FOR SEQ ID NO:3:

( i ) SEQUENCE CHARACTERISTICS:
        ( A ) LENGTH: 1497 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i i ) IMMEDIATE SOURCE:
        ( B ) CLONE: BILE ACID SULFATASE ( i x ) FEATURE:
        ( A ) NAME/KEY: CDS
        ( B ) LOCATION: 106..1509

( x i ) SEQUENCE DESCRIPTION: SEQ ID NO:3:

```
ATGGCAAACA TGAGAAAAGT ATCTCGCCTC TCCCGATACG CCTTTGCCAC AGCCCTGGCA      60
CTGAGCCAGT TCGGCACAGG CACGGCCAAC GCCCACGATC AGGATGATCG CGGTGGCTCG     120
GGAGCGAAAA GCCCCGCTGT GCTTGCTGCC CGCGCCCAGG TGTTCAAGGC CAATCCGCAG     180
ATGGTCAGGT CCATCATGGA AGGCGGTGGC TTTGGCACCG AGCTGTCGTA TGCAGTAGCC     240
AACAGCATGT ACAGCCGAAC CGACCAGAAC GCCATTGCAG ATGCCCGAGC CAAGCTCAAA     300
GTCGAGGCCG TGGCTCCACG CACCTGGCTG CTGCGTTTCC CCATCGTCAA CGTGGTGGTC     360
TTCGAGACCG ACGAAGGCCT GGTCTTGGTC GATAGCGGCT ACGCACCTGC AGGCCCGGCC     420
TTGGCCGAAA CGCTGAAGAA GCTCAGCAAC AAGCCGTTGC ACACCGTCAT CCTCACGCAC     480
TTTCATGCCG ACCATGCCTT TGGCGCCTGG GCGTTGATGG ACCAGAAGCC GCATGTAGTG     540
ACCGAGCAGC GCTTCATCTC CAGATGGAG CTGGACATGC GCAGCAACGG TCTGATTGCA     600
CGCAACAACC AGCAAAGCGT GGCCGATGTG CCCCGGACCT GGGCAGATGC AGTTCGGCCC     660
ACCCAGACCT TCAGGGACAA GACCACACTC AAAATTGGCG GCGAAGACTT TGTGCTGACC     720
CATGCGCGCG GCGAGACCGA AGACCAGATA TGGGTTGCCG TTCCAGGCCG GAAAATCGTG     780
GCCAGCGCGG ATTATTTCCA GGGGTTTCTG CCCAATGCGG GCAACGGCAA GCGCCGCCAG     840
CGCTACCCCG AGGAGTGGGC CCGGGCCCTG CGCGACATGG CAGCACTCAA ACCCGAGCTG     900
CTGCTGCCGG CGCATGGTCC GGCCATCACC AAGCCCGAGG AAATTCAGGA CCGACTGCCC     960
GCCCAGGCCC AGATGCTGGA CAGCATCTCC AGGCAAGTGG TGGCCGGCCT GAACAGCGGA    1020
GTACGCCGCG ATCAGGTCAT TGAAAAAGTC GCACTGCCGC CGGAGCTGGC CCGGCGAAGC    1080
GATGCACGCG AGCTATATGT GTCTGCCAAA GACATAGGCC GCATGGTGGT CAGCGAGTAC    1140
AGCGGCTGGT GGACGATAT TCCATCGCAC TGGCGCCCGG CGTCCCTGGC CAATGAGGCC    1200
AAAGAAATCG TGCAGCTAGC TGGCGGTGCC AGGCCGGTGA TTCAGCGTGC AGTGGCGCTG    1260
GCAGACAGCA ATCCGGAGCT GGCCTCCCAT CTGGCCGACT GGGCCTGGTA TGCAGACAGC    1320
GATGACACCG AGGTGGCTCA AGGCGCACTG AAGGTCTATT CCGCGCGTGT TGCCAAGCCT    1380
CTGCCCACGC AGGAAGTGCT GGTCTATGCC GAGCACATGG TGCGCCTGCA GCTCAAGCTC    1440
AATGAGCTGA ACAGCACACG CGCGGCCAGC GCCAGTCAGA GCAGCAAAGC GCATTAA      1497
```

( 2 ) INFORMATION FOR SEQ ID NO:4:

( i ) SEQUENCE CHARACTERISTICS:
        ( A ) LENGTH: 1488 base pairs ( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v i i ) IMMEDIATE SOURCE:
( B ) CLONE: BILE ACID SULFATASE ( i x ) FEATURE:
( A ) NAME/KEY: CDS
( B ) LOCATION: 106..1509

( x i ) SEQUENCE DESCRIPTION: SEQ ID NO:4:

| | | | | | | |
|---|---|---|---|---|---|---|
| ATGAGAAAAG | TATCTCGCCT | CTCCCGATAC | GCCTTTGCCA | CAGCCCTGGC | ACTGAGCCAG | 60 |
| TTCGGCACAG | GCACGGCCAA | CGCCCACGAT | CAGGATGATC | GCGGTGGCTC | GGGAGCGAAA | 120 |
| AGCCCCGCTG | TGCTTGCTGC | CCGCGCCCAG | GTGTTCAAGG | CCAATCCGCA | GATGGTCAGG | 180 |
| TCCATCATGG | AAGGCGGTGG | CTTTGGCACC | GAGCTGTCGT | ATGCAGTAGC | CAACAGCATG | 240 |
| TACAGCCGAA | CCGACCAGAA | CGCCATTGCA | GATGCCCGAG | CCAAGCTCAA | AGTCGAGGCC | 300 |
| GTGGCTCCAC | GCACCTGGCT | GCTGCGTTTC | CCCATCGTCA | ACGTGGTGGT | CTTCGAGACC | 360 |
| GACGAAGGCC | TGGTCTTGGT | CGATAGCGGC | TACGCACCTG | CAGGCCCGGC | CTTGGCCGAA | 420 |
| ACGCTGAAGA | AGCTCAGCAA | CAAGCCGTTG | CACACCGTCA | TCCTCACGCA | CTTTCATGCC | 480 |
| GACCATGCCT | TTGGCGCCTG | GGCGTTGATG | GACCAGAAGC | CGCATGTAGT | GACCGAGCAG | 540 |
| CGCTTCATCT | CCCAGATGGA | GCTGGACATG | CGCAGCAACG | GTCTGATTGC | ACGCAACAAC | 600 |
| CAGCAAAGCG | TGGCCGATGT | GCCCCGGACC | TGGGCAGATG | CAGTTCGGCC | CACCCAGACC | 660 |
| TTCAGGGACA | AGACCACACT | CAAAATTGGC | GGCGAAGACT | TTGTGCTGAC | CCATGCGCGC | 720 |
| GGCGAGACCG | AAGACCAGAT | ATGGGTTGCC | GTTCCAGGCC | GGAAAATCGT | GGCCAGCGCG | 780 |
| GATTATTTCC | AGGGGTTTCT | GCCCAATGCG | GGCAACGGCA | AGCGCCGCCA | GCGCTACCCC | 840 |
| GAGGAGTGGG | CCCGGGCCCT | GCGCGACATG | GCAGCACTCA | AACCCGAGCT | GCTGCTGCCG | 900 |
| GCGCATGGTC | CGGCCATCAC | CAAGCCCGAG | GAAATTCAGG | ACCGACTGCC | CGCCCAGGCC | 960 |
| CAGATGCTGG | ACAGCATCTC | CAGGCAAGTG | GTGGCCGGCC | TGAACAGCGG | AGTACGCCGC | 1020 |
| GATCAGGTCA | TTGAAAAAGT | CGCACTGCCG | CCGGAGCTGG | CCCGGCGAAG | CGATGCACGC | 1080 |
| GAGCTATATG | TGTCTGCCAA | AGACATAGGC | CGCATGGTGG | TCAGCGAGTA | CAGCGGCTGG | 1140 |
| TGGGACGATA | TTCCATCGCA | CTGGCGCCCG | GCGTCCCTGG | CCAATGAGGC | CAAAGAAATC | 1200 |
| GTGCAGCTAG | CTGGCGGTGC | CAGGCCGGTG | ATTCAGCGTG | CAGTGGCGCT | GGCAGACAGC | 1260 |
| AATCCGGAGC | TGGCCTCCCA | TCTGGCCGAC | TGGGCCTGGT | ATGCAGACAG | CGATGACACC | 1320 |
| GAGGTGGCTC | AAGGCGCACT | GAAGGTCTAT | TCCGCGCGTG | TTGCCAAGCC | TCTGCCCACG | 1380 |
| CAGGAAGTGC | TGGTCTATGC | CGAGCACATG | GTGCGCCTGC | AGCTCAAGCT | CAATGAGCTG | 1440 |
| AACAGCACAC | GCGCGGCCAG | CGCCAGTCAG | AGCAGCAAAG | CGCATTAA | | 1488 |